US 9,039,656 B2

(12) United States Patent
Vanderveen et al.

(10) Patent No.: US 9,039,656 B2
(45) Date of Patent: May 26, 2015

(54) MEDICATION SAFETY ENHANCEMENT FOR SECONDARY INFUSION

(71) Applicant: CareFusion 303, Inc., San Diego, CA (US)

(72) Inventors: Timothy W. Vanderveen, Poway, CA (US); Robert D. Butterfield, Poway, CA (US)

(73) Assignee: CAREFUSION 303, INC., San Diego, CA (US)

(*) Notice: Subject to any disclaimer, the term of this patent is extended or adjusted under 35 U.S.C. 154(b) by 0 days.

(21) Appl. No.: 14/161,661

(22) Filed: Jan. 22, 2014

(65) Prior Publication Data

US 2014/0142545 A1 May 22, 2014

Related U.S. Application Data

(63) Continuation of application No. 10/750,345, filed on Dec. 31, 2003, now Pat. No. 8,672,875.

(51) Int. Cl.
A61M 31/00 (2006.01)
A61M 5/50 (2006.01)
A61M 5/168 (2006.01)
A61M 5/142 (2006.01)

(52) U.S. Cl.
CPC ......... *A61M 5/5086* (2013.01); *A61M 5/16827* (2013.01); *A61M 5/14212* (2013.01); *A61M 5/16854* (2013.01); *A61M 2205/3351* (2013.01)

(58) Field of Classification Search
USPC .................. 604/67, 81, 80; 137/109
See application file for complete search history.

(56) References Cited

U.S. PATENT DOCUMENTS

| 4,394,862 | A | 7/1983 | Shim |
| 4,430,074 | A | 2/1984 | Mooring |
| 4,530,696 | A | 7/1985 | Bisera et al. |
| 4,533,347 | A | 8/1985 | Deckert |
| 4,553,958 | A | 11/1985 | LeCocq |
| 4,617,014 | A | 10/1986 | Cannon et al. |
| 4,650,464 | A | 3/1987 | Ruiz et al. |
| 4,673,389 | A | 6/1987 | Archibald et al. |
| 4,681,563 | A | 7/1987 | Deckert et al. |
| 4,696,671 | A | 9/1987 | Epstein et al. |

(Continued)

FOREIGN PATENT DOCUMENTS

| EP | 0361662 A1 | 4/1990 |
| JP | 3173574 A | 7/1991 |

(Continued)

*Primary Examiner* — Nicholas Lucchesi
*Assistant Examiner* — Deanna K Hall
(74) *Attorney, Agent, or Firm* — McDermott Will & Emery LLP

(57) ABSTRACT

A system and method determine when fluid is not flowing properly from a secondary infusion source during a secondary infusion. The system includes an upstream pressure sensor and a processor programmed to receive signals from the sensor and analyze the signals to determine if secondary fluid flow is proper. The processor samples the output signals from the upstream pressure sensor and analyzes the sampled signals to determine if a pressure rise in the infusion line has occurred when the secondary infusion is initiated. If a pressure rise, indicating that fluid from the secondary container has begun flowing into the infusion line, has not been detected, the processor is programmed to provide a signal indicating that attention should be given to the infusion set up.

20 Claims, 6 Drawing Sheets

(56) References Cited

U.S. PATENT DOCUMENTS

| | | |
|---|---|---|
| 4,705,506 A | 11/1987 | Archibald |
| 4,710,166 A | 12/1987 | Thompson et al. |
| 4,714,463 A | 12/1987 | Archibald et al. |
| 4,769,001 A | 9/1988 | Prince |
| 4,816,019 A | 3/1989 | Kamen |
| 4,828,545 A | 5/1989 | Epstein et al. |
| 4,836,752 A | 6/1989 | Burkett |
| 4,838,856 A | 6/1989 | Mulreany et al. |
| 4,850,972 A | 7/1989 | Schulman et al. |
| 4,865,584 A | 9/1989 | Epstein et al. |
| 4,882,575 A | 11/1989 | Kawahara |
| 4,898,576 A | 2/1990 | Philip |
| 4,938,072 A | 7/1990 | Brown et al. |
| 4,946,439 A | 8/1990 | Eggers |
| 4,979,940 A | 12/1990 | Bobo, Jr. et al. |
| 4,998,914 A | 3/1991 | Wiest et al. |
| 5,032,112 A | 7/1991 | Fairchild et al. |
| 5,087,245 A | 2/1992 | Doan |
| 5,088,981 A | 2/1992 | Howson et al. |
| 5,096,385 A | 3/1992 | Georgi et al. |
| 5,100,380 A | 3/1992 | Epstein et al. |
| 5,108,367 A | 4/1992 | Epstein et al. |
| 5,154,700 A | 10/1992 | Dansby |
| 5,304,126 A | 4/1994 | Epstein et al. |
| 5,312,334 A | 5/1994 | Hara et al. |
| 5,356,378 A | 10/1994 | Doan |
| 5,423,743 A | 6/1995 | Butterfield |
| 5,423,749 A | 6/1995 | Merte et al. |
| 5,439,355 A | 8/1995 | Jimison et al. |
| 5,464,392 A | 11/1995 | Epstein et al. |
| 5,554,115 A | 9/1996 | Thomas et al. |
| 5,803,917 A | 9/1998 | Butterfield et al. |
| 5,935,106 A | 8/1999 | Olsen |
| RE36,871 E | 9/2000 | Epstein et al. |
| 6,213,972 B1 | 4/2001 | Butterfield et al. |
| 6,358,225 B1 | 3/2002 | Butterfield |
| 2001/0023345 A1 | 9/2001 | Wolff et al. |

FOREIGN PATENT DOCUMENTS

| | | |
|---|---|---|
| JP | 6233818 A | 8/1994 |
| JP | 2004-266186 | 9/2004 |
| WO | WO-01/43798 A1 | 6/2001 |
| WO | WO-01-78808 | 10/2001 |

MEDICATION SAFETY ENHANCEMENT FOR SECONDARY INFUSION

CROSS-REFERENCE TO RELATED APPLICATIONS

The present application claims the benefit of priority under 35 U.S.C. §120 as a continuation from U.S. patent application Ser. No. 10/750,345 entitled "Medication Safety Enhancement for Secondary Infusion," filed on Dec. 31, 2003, the disclosure of which is hereby incorporated by reference in its entirety for all purposes.

BACKGROUND OF THE INVENTION

1. Field of the Invention

The present invention generally relates to a system and method for determining whether a secondary infusion has been properly set up and administered. More specifically, the present invention relates to a system including an infusion pump having a sensor that is capable of monitoring and detecting pressure within the container-side of a fluid infusion set. The pressure sensor is used to monitor the pressure within the container-side of the infusion set and provides signals that may be analyzed by a processor to determine, for example only, and not by way of limitation, whether a check-valve in a primary infusion line is working properly, whether the differential height of the primary and secondary fluid containers is correct, and whether a manual valve in the secondary infusion line has been opened and generally whether the secondary infusion line provides an unobstructed flow path to the secondary fluid container. The processor is programmed to provide a signal to care-givers in an institution, or store a record of the event in an institutional database, in response to determining that a fault in the infusion set up has been detected.

2. General Background and State of the Art

Infusion of therapeutic fluids to treat or nourish patients is commonly used in hospitals and other medical care institutions. Originally, such infusions were carried out by hanging a bag or container of therapeutic fluid from a pole so that fluid flows under the force of gravity regulated by a user-controllable restrictor through a length of tubing and into the lumen of a vessel of a patient. More recently, the flow of fluid into the patient is accomplished under the control of a programmed infusion pump located in the fluid pathway. Infusion pumps are useful in that they allow for more precise control of the low of therapeutic fluid into the patient. For example, using an infusion pump, relatively precise amounts of fluid may be infused at controlled rates. Moreover, the rate of infusion may be altered during the infusion by programming the pump to pump the fluid at a different rate. This capability is useful where a bolus of therapeutic fluid is desired to initiate an infusion regimen, with the rate then being decreased to a reduced flow rate for the remainder of the infusion.

Although standard infusion sets have typically provided for the administration of a single fluid, the need to administer two different fluids to a patient is not uncommon. Typically, such a need arises when a patient must have a maintenance solution delivered and, concomitantly with the administration of the maintenance fluid, there is a need for the intermittent infusion of a therapeutic solution. In such cases it has been the practice to use what is commonly referred to as a "piggyback" system wherein separate fluids from separate containers are sequentially infused through a common tube. Such systems have several obvious advantages. For instance, in a piggyback system the needle need not be removed from the patient whenever the administration of fluids changes from the maintenance solution to the therapeutic solution or vice versa. This fact, of course, causes less trauma to the patient, avoids unnecessary pain, and reduces the chances of infection. Furthermore, and equally important, the use of a piggyback system simplifies procedures for the nurse.

Several devices are employed in the sequential administration of two separate solutions to a patient. Basically, these systems comprise a primary administration set and a secondary administration set and rely on the varying differential of hydrostatic pressure at a check valve throughout the course of delivery for the sequencing of fluid flow within the system.

When the secondary container is set up, the primary container is typically placed below of the level of the secondary container, generally approximately eight inches below the primary container. The primary container may be left in this position, or it may be raised once the secondary container has emptied. Normally, a one-way check valve is included in the infusion line connecting the primary container to the infusion pump, and the infusion line from the secondary container is connected to the infusion line at a location below, or downstream, of the check valve. This check valve prevents therapeutic fluid from the secondary container from flowing upwards into the primary container, and may also be set to prevent flow of fluid from the primary container while fluid is flowing from the secondary container.

One problem occurs when the secondary container is incorrectly placed at or below the level of the primary container. When this happens, the differential hydrostatic pressure which would normally close the one-way check valve is non-existent. If the containers are so improperly placed, fluid from both the primary and secondary containers may flow into the pump concurrently, or if the secondary container is sufficiently lower than the primary container then primary fluid may flow into the secondary container. In either case, where the primary fluid and secondary fluid are incompatible, or if the infusion regimen calls for one the fluids to be sequentially infused in a necessary order, attention must be given to the infusion set up to correct the problem. Unfortunately, this problem may go un-noticed by a busy care-giver.

Typically, a manual valve (roller clamp, slide clamp etc.) is included in the secondary infusion line between the secondary container and the connection of the secondary infusion line to the infusion line that is connected to the pump. This valve is useful in that it allows for connection of the secondary fluid container to the infusion set up while infusion from the primary fluid is being infused, and is opened only when it is time to begin infusion from the secondary container. A problem occurs when the care-giver fails to open this valve, thus preventing the secondary infusion fluid from being pumped from the secondary container, in this situation the primary fluid will be infused at the secondary flow rate which may cause undesired medical consequences.

An additional problem occurs when the containers are in their proper position for automatic secondary infusion but the one-way check valve fails allowing fluid to flow bi-directionally. When this happens, fluid from the secondary container, because the secondary container is higher than the level of the primary container, and thus has a greater hydrostatic pressure than the fluid in the primary container may flow into the primary container, mixing with the primary fluid. This is disadvantageous for the reasons stated previously.

Still another potential problem in the administration and set up of a secondary infusion occurs when multiple fault conditions exist simultaneously. One such condition consists of a bidirectionally open one-way check valve fault and the manual valve on the secondary infusion line being inadvertently closed when it is intended to be open for secondary delivery.

Often, the secondary container is filled with a volume different from the volume that is programmed to be delivered. Typically, the pump is programmed with a "secondary" volume to be infused. Where the secondary container is overfilled, a volume of secondary fluid remains in the secondary container when the pump determines that the secondary volume to be infused parameter has been satisfied. When this happens, the pump, which may have been programmed to change its pumping rate when the secondary infusion is completed, begins pumping the remaining secondary fluid at the new rate, which may be too high a rate for the particular secondary fluid being infused.

Similarly, where the secondary container has been underfilled, the pump will exhaust the secondary container before the volume to be infused parameter is satisfied, and will continue pumping at the secondary infusion rate. However, due to the exhaustion of the fluid within the secondary container, the one-way check valve will open, and allow fluid from the primary container to flow into the infusion line. Thus, the pump may continue to pump primary infusion fluid at the secondary flow rate, this flow rate may be inappropriate for the primary fluid.

What has been needed and heretofore unavailable, is a simple and reliable system and method for detecting when an infusion container is empty, or nearly empty, and for providing a signal to an infusion pump to either alter the infusion rate, provide an alert signal to a care-giver that the container needs replenishment or replacement. Such a system should be able to detect when the height of the secondary infusion container is incorrect relative to the height of the primary infusion container, and should also be able to detect when the manual valve or clamp on the secondary infusion line has not been opened under the desired mode of operation. The system should also be capable of detecting a failure of the one-way valve, as well as certain multiple fault conditions. The present invention satisfies these and other needs.

INVENTION SUMMARY

Briefly and in general terms, the present invention is directed to a system and method for monitoring the status of a secondary infusion administration and providing an alert to caregivers that the infusion set up requires attention when it is determined that the secondary infusion is not functioning correctly. More specifically, in one aspect in accordance with the invention, a system and method are provided for monitoring the pressure in an upstream infusion line to determine if the pressure within the infusion line increases beyond a predetermined threshold after initiation of a secondary infusion. If the pressure does not increase beyond the threshold, the system determines that the infusion is not functioning correctly and provides an alert to care-givers to that effect.

The system and method of the present invention are advantageous in that they allow detection of various faults that occur during the administration of a secondary infusion. For example, the system and method of the present invention provide for detecting when a secondary infusion is started without opening a valve in the secondary infusion line, when the secondary infusion container is positioned at or below the level of the primary infusion container, when a check valve in the primary infusion line is defective and when certain multiple fault conditions exists, specifically when the valve in the secondary infusion line is not opened and the check valve is open bi-directionally. The system and method also provide for detecting when the secondary container has emptied, thereby helping to prevent problems associated with under- or over-filling of the secondary container.

In one aspect, the method of the present invention includes a passive monitoring system that samples the pressure within an upstream infusion line after a secondary infusion is initiated. The sampled pressure is compared to a threshold pressure, and if the sampled pressure is greater than or equal to the threshold pressure, an alert is provided. In another aspect, the method includes determining whether the sampled pressure was sampled during a measurement window before comparing the sampled pressure to the threshold pressure.

In another aspect of the present invention, an active monitoring system and method includes establishing a baseline pressure and then controllably increasing and decreasing the volume of fluid within the upstream infusion line. The pressure within the upstream line is sampled after the volume increase, and a characteristic of the sampled pressure is determined, and then compared with a characteristic of a threshold pressure. An alert is provided if the determined characteristic is greater than or equal to the characteristic of the threshold pressure.

In yet another aspect of the present invention, aspects of the passive monitoring system and the active monitoring systems are combined. This is advantageous in determining overfill and underfill conditions of the secondary infusion container. Additionally, in another aspect, the active monitoring mode is carried out only if the passive monitoring mode indicates that a fault condition exists. This is advantageous in that the increase of volume within the upstream infusion line may, in some mechanism designs, result in a concomitant change in the output of the infusion pump that is not desirable. Operating the active mode only if the passive mode indicates a fault minimizes the use of the active mode to confirming the results of the passive monitoring mode. In some cases, such operation also provides an opportunity to adjust the infusion set up to improve the sensitivity of the passive monitoring mode.

In yet another aspect, the present invention comprises a system for determining a fault condition in an infusion system including an infusion pump capable of infusing fluid from a primary container connected to a primary infusion line and a secondary container connected to the primary infusion line through a secondary infusion line, the secondary infusion line having a valve to control flow of the secondary fluid in the secondary fluid line, the primary infusion line having a check valve disposed between the primary container and the connection of the secondary infusion line to the primary infusion line, the check valve configured to prevent flow toward the primary container from the primary infusion line, the system comprising a pressure sensor disposed adjacent the primary infusion line below the connection of the secondary infusion line to the primary infusion line, the pressure sensor in operative arrangement with the primary infusion line to measure pressure within the primary infusion line, the pressure sensor providing signals representative of the fluid pressure within the primary infusion line; a memory for storing pressure related values; a processor in communication with the memory and responsive to the signals provided by the pressure sensor, the processor programmed to sample the pressure signals, establish a baseline pressure value, store the baseline pressure value in the memory, compare the baseline pressure value with pressure values sampled at a latter time, and if the latter sampled pressure value equals or is not greater than a selected passive detection threshold pressure value, provide an alert that a fault condition exists.

In another aspect, the processor determines if the time of the latter sampled pressure value is within a measurement window before comparing the latter sampled pressure value to the passive detection threshold pressure value, the window having a start boundary and an end boundary, and if the latter sampled pressure value has been sampled at a time within the start and end boundaries, and the latter sampled pressure value is not equal to or greater than the selected passive detection pressure value, the alert is provided.

In still another aspect, the processor is further programmed to operate the infusion pump in a reverse mode to inject a bolus of fluid into the intake side primary infusion line after measuring the baseline pressure value. In another aspect, the processor is programmed to operate the infusion pump in a reverse mode to inject a bolus of fluid into the primary infusion line only if the latter sampled pressure value is less than the selected passive detection threshold pressure value.

In a further aspect of the present invention, the processor is programmed to sample the pressure signals received from the pressure sensor after operating the infusion pump in the reverse mode, and analyze the pressure signals to determine a characteristic of a pressure wave represented by the pressure signals, and compare that characteristic with a baseline characteristic of the stored baseline pressure value, and if the characteristic is equal to or greater than a selected active detection threshold, provide an alert indicating that a fault condition exists. In still a further aspect, if the characteristic is less than the selected active detection threshold, the processor provides a "CHECK SET UP" alert to a care-giver.

In another aspect, the present invention includes a system for determining a fault condition in an infusion system including an infusion pump capable of infusing fluid from a primary container connected to a primary infusion line and a secondary container connected to the primary infusion line through a secondary infusion line, the secondary infusion line having a manually operated valve to control flow of the secondary fluid in the secondary fluid line, the primary infusion line having a check valve disposed between the primary container and the connection of the secondary infusion line to the primary infusion line, the check valve for prevent flow backwards from the primary infusion line into the primary container, the system comprising a pressure sensor disposed adjacent the primary infusion line below the connection of the secondary infusion line to the primary infusion line, the pressure sensor in operative engagement with the primary infusion line to measure pressure within the primary infusion line, the pressure sensor providing signals representative of the pressure within the primary infusion line; a memory for storing pressure related values; and a processor in communication with the memory and responsive to the signals provided by the pressure sensor, the processor programmed to sample the pressure signals, establish a baseline pressure value, store the baseline pressure value in the memory, operate the infusion pump to increase the pressure in the primary infusion line, sample the pressure signals after operating the pump to increase the volume in the primary infusion line, compare the baseline pressure value with pressure values sampled after operating the pump to increase the volume in the primary infusion line, and if the latter sampled pressure value equals or is greater than a selected active detection threshold pressure value, provide an alert that a fault condition exists.

In a more detailed aspect, the processor operates the pump in a reverse mode to increase the fluid volume in the primary infusion line. In another aspect, the system further includes a controllable device for applying displacement to the primary infusion line, the device disposed between an intake of the infusion pump and the connector connecting the secondary infusion line to the primary infusion line. In yet another aspect, the controllable device is responsive to signals from the processor to apply displacement to the primary infusion line reducing its interval volume capacity.

In another aspect, the present invention is embodied in a method of determining whether a manually operated valve in a secondary infusion line is properly opened during a secondary infusion; comprising sampling pressure signals provided by a pressure sensor in operable communication with an upstream infusion line; establishing a baseline pressure from the sampled pressure signals; storing the baseline pressure in a memory; sampling further pressure signals after establishing the baseline pressure; comparing the further sampled pressure to the baseline pressure; and providing an alert if a further sampled pressure value is equal to or greater than a passive detection threshold pressure. In a further aspect, the method of the present invention includes determining if the further sampled pressure value was sampled at a time occurring within a selected measurement window having a start time and an end time.

In yet another aspect, the method of the present invention includes causing an increase in the volume within the upstream infusion line if the further sampled pressure value is less than the passive detection threshold pressure; sampling the pressure signals after the volume in the primary infusion line is increased; comparing a characteristic of the pressure signals sampled after the pressure in the primary infusion line is increased with a characteristic of the active detection threshold pressure; and providing an alert if the characteristic of the pressure signals is greater than or equal to the characteristic of the active detection threshold pressure. In a further more detailed aspect, the step of sampling the pressure signals after the pressure is increased includes integrating the characteristic with respect to the baseline pressure and comparing the integrated characteristic with the characteristic of the active detection threshold pressure.

In a still further aspect, the present invention includes a method for determining the status of a secondary infusion; comprising sampling pressure signals provided by a pressure sensor in operable communication with an upstream infusion line; establishing a baseline pressure from the sampled pressure signals; storing the baseline pressure in a memory; causing an increase in the volume within the upstream infusion line; sampling the pressure signals after the volume in the primary infusion line is increased; comparing a characteristic of the pressure signals sampled after the volume in the primary infusion line is increased with a characteristic of the threshold pressure; and providing an alert if the characteristic of the pressure signals is greater than or equal to the characteristic of the active detection threshold pressure. In one additional aspect, the step of causing an increase in the volume within the upstream infusion line includes operating an infusion pump in a reverse mode. In another aspect, the step of causing an increase in the volume within the upstream infusion line includes controlling a device to transiently decrease the contained capacity of the upstream infusion line. In still another aspect, the device comprises an electromechanical actuator and the step of reducing the capacity within the upstream infusion line includes controlling the electromechanical actuator to squeeze and release the upstream infusion line.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
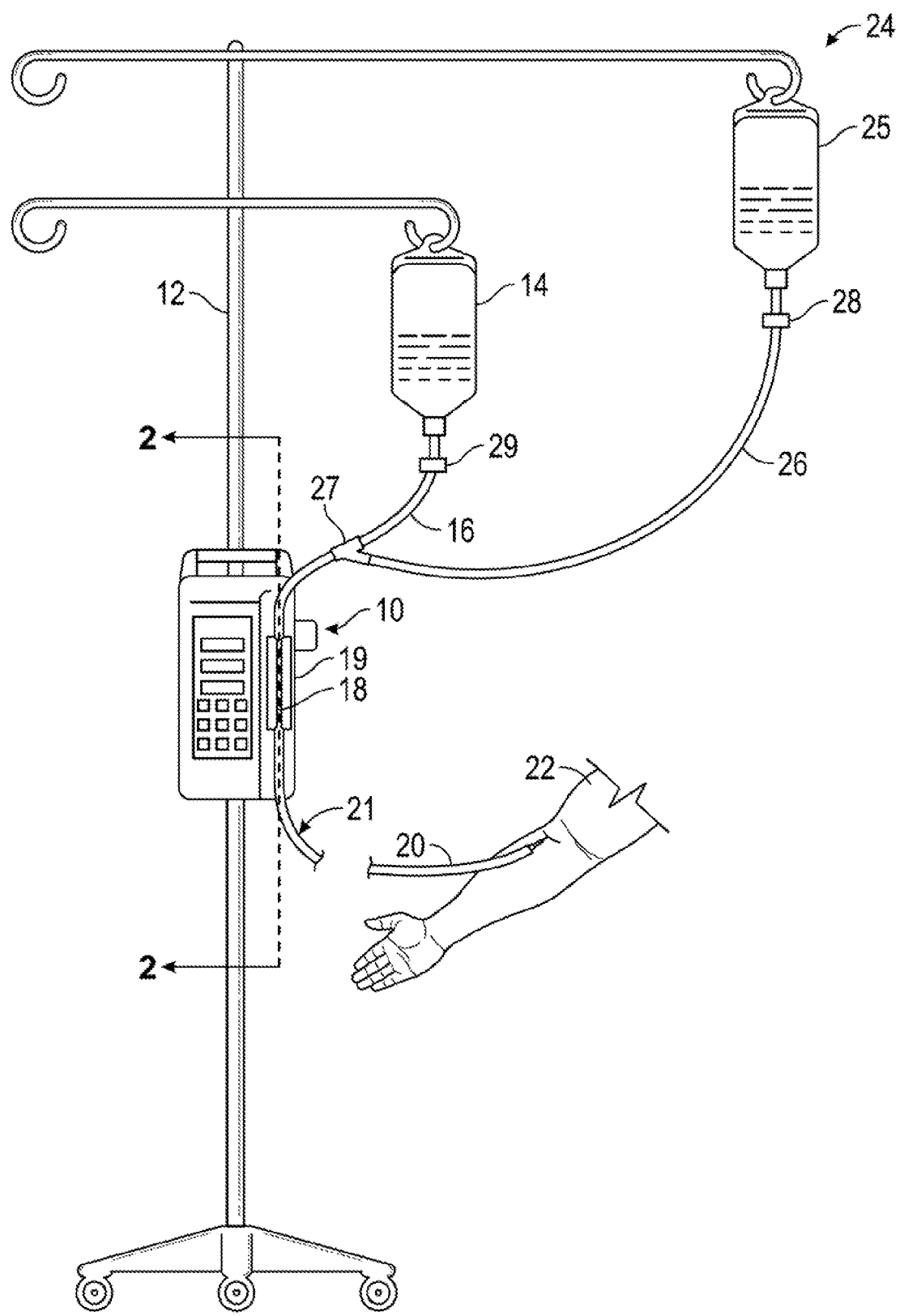
FIG. 1 depicts an infusion set-up including primary and secondary fluid sources and associated valves and an infusion pump for infusing fluid from the fluid sources into a patient.

Referring now to the drawings in detail, in which like reference numerals indicate like or corresponding elements among the several figures, there is shown in FIG. 1 an infusion pump set-up, generally designated 10, shown in use in its intended environment. In particular, the infusion pump set-up 10 is shown mounted to an intravenous (I.V.) pole 12 on which a fluid source 14 containing an I.V. fluid is held. The fluid source 14 is connected in fluid communication with an upstream fluid line 16. The fluid line 16 is a conventional I.V. infusiontype tube typically used in a hospital or medical environment, and is made of any type of flexible tubing appropriate for use to infuse therapeutic fluids into a patient, such as polyvinylchloride (PVC). A flexible pumping fluid line 18 is mounted in operative engagement with a peristaltic pumping apparatus 19, for propelling fluid through a downstream fluid line 20, for example, to a patient's arm 22. It will be understood by those skilled in the art that the upstream fluid line 16, the flexible line 18, and the downstream fluid line 20 may be portions of a continuous length of flexible tubing, with the portions defined by the location of the peristaltic pump 19. For convenience, the continuous length of flexible tubing is indicated by numeral 21. In this context, the term "upstream" refers to that portion of the flexible tubing that extends between the fluid source and peristaltic pump, and the term "downstream" refers to that portion of the flexible tubing that extends from the peristaltic pump to the patient.

Also shown in FIG. 1 is a secondary administration setup generally indicated by numeral 24. The secondary administration setup 24 includes a secondary fluid container 25 that may be filled with a second therapeutic fluid for infusion into the patient 22. Fluid from the secondary fluid container 25 flows through a secondary fluid line 26 into the fluid line 16 through a connector 27. A manually operated valve 28 is located in the secondary line 26 to control the flow of fluid flowing out of the secondary container 25 into the upstream fluid line 16. The one-way check valve 29 is disposed in the upstream fluid line 16 between the primary fluid container 14 and the connector 27, the one-way check valve is configured so that when the elevation of the fluid in the secondary container 25 is greater than that of the primary container, the differential pressure within line 16 closes the check valve and prevents secondary fluid from flowing into the primary container 14, and also prevents fluid from flowing out of primary container 14. Thus, the check valve 29 generally prevents mixing of the primary and secondary infusion fluids.

Figure 2:
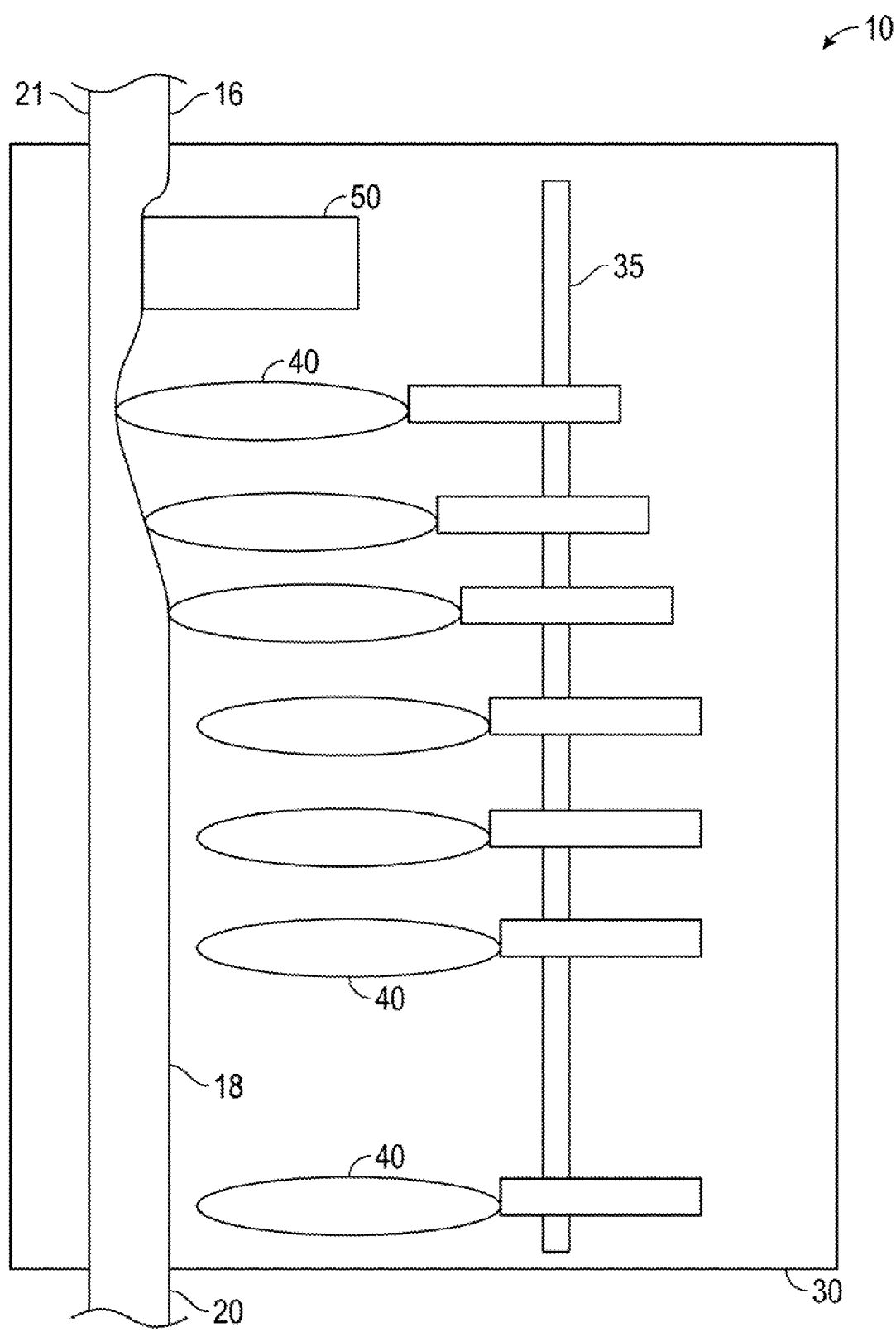
FIG. 2 is a schematic side view of an exemplary peristaltic infusion pump including an upstream pressure sensor.

FIG. 2 depicts an enlarged view of the pumping mechanism of the infusion pump 10 showing the interaction of the upstream tube 16 with the elements of the peristaltic infusion pump. The upstream fluid line 16 is disposed in the housing 30 of the pump 10 in such a manner that the pumping line 18 is in releasable contact with one or more fingers 40 of the peristaltic infusion pump. Typically, such a peristaltic infusion pump utilizes a camshaft 35 or other mechanism to actuate one or more pumping fingers 40 so that one or more of the pumping fingers 40 sequentially press upon and squeeze the pumping line 18 to displace fluid within the tube in a downstream direction.

An upstream pressure sensor or detector 50 is mounted in the housing of the pump 10 to monitor the fluid pressure within the upstream tube 16. The upstream pressure sensor 50 may be any kind of detector known in the art that is capable of monitoring the fluid pressure within the upstream tube 16 and providing signals that may be received by suitable electronics, such as, for example an amplifier, an A/D converter, and a storage medium, such as a flash memory or other type of suitable storage medium for storing digital values representative of the signals provided by the sensor. The signals may also be provided to a computer or microprocessor for analysis, display, or reporting. Examples of pressure sensors or detectors suitable for monitoring the pressure within an upstream infusion line are silicon strain gauges, resistive strain beams, or other sensors or detectors known to those skilled in the art.

Those skilled in the art will also understand that the upstream pressure sensor and method embodied in the present invention are equally applicable to any displacement type infusion pump, and such is intended to be within the scope of the present invention. Even further, the principles may be employed even in pumps or servo-controlled gravity flow regulators. Moreover, while the present invention is described in relation to an infusion pump having a processor or computer associated with the pump, it is intended that the invention also include systems wherein the microprocessor or computer is remote from, but in communication with the pump.

Figure 3:
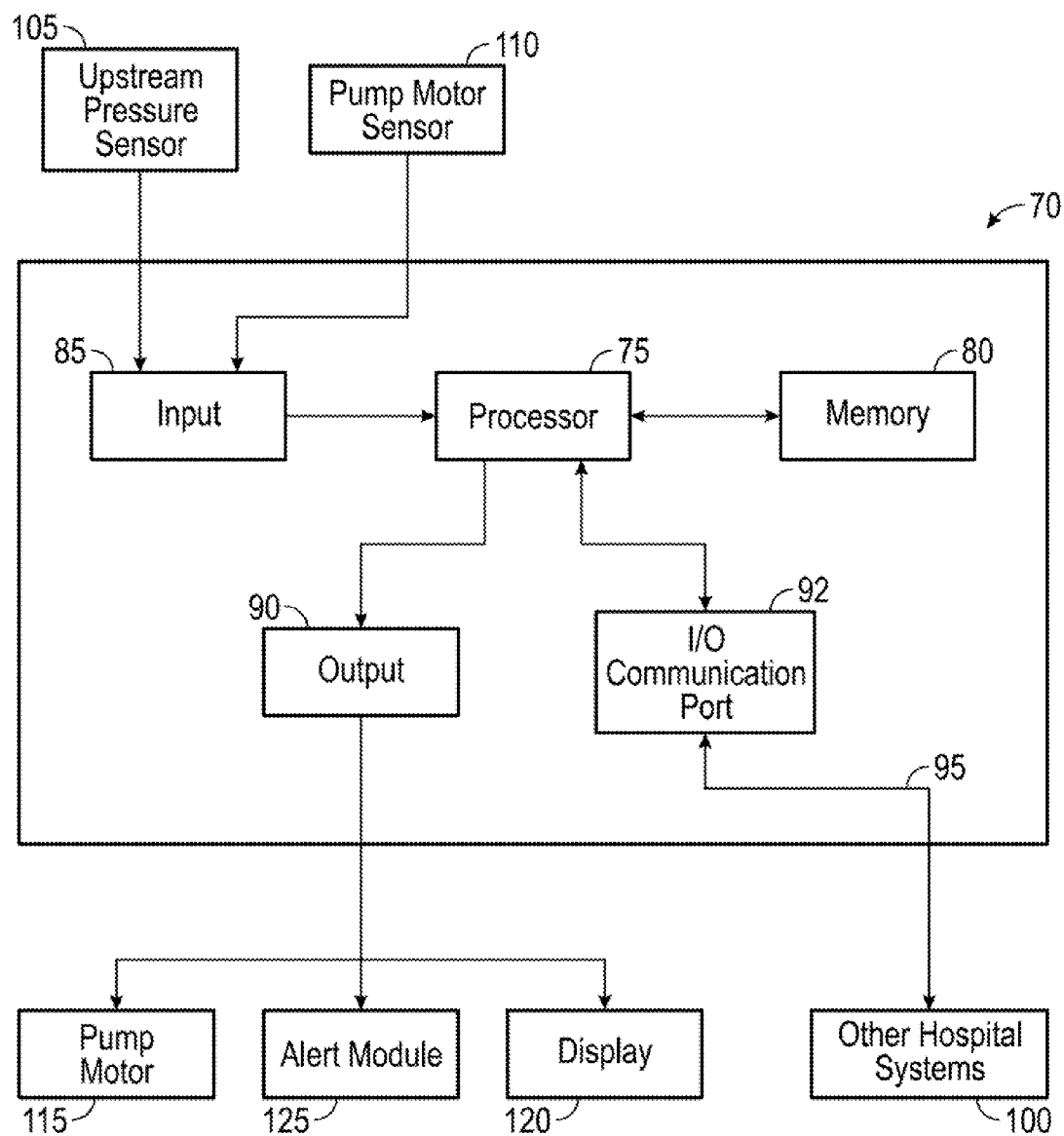
FIG. 3 is a schematic block diagram of one embodiment of an infusion pump controller capable of being programmed to provide a system in accordance with aspects of the invention and to carry out the methods of the present invention.

Generally, as shown in FIG. 3, the infusion pump will include a control system 70 configured or programmed to control the operation of the peristaltic infusion pump so that a prescribed amount of medication or other therapeutic fluid is infused into the patient over a desired period of time. Such control systems typically include a microprocessor 75, a memory 80 associated with the microprocessor 75, one or more inputs 85 for inputting signals to the microprocessor, and one or more outputs 90 for outputting signals from the microprocessor.

The control system 70 may also be in communication with other systems, such as a pharmacy information system, hospital administration system, or other such systems in the institution using an input/output communications port 92 and a communication means 95. The input/output communications port 92 may be any port configured to send and receive data using appropriate communication protocols, such as RS232 and the like. For example, the input/output communications port 92 may be a serial port, a parallel port, a USB, or other suitable port. It will also be understood that the input 85 and the output 90 may be combined in such a manner that all signals to and/or from the processor are communicated through one or more input/output ports 92, rather than through separate inputs and outputs.

The communication means 95 may be a hard wired or wireless connection to another computer, a local area network, a wide area network, a telephone line to a remote server or client system, or the Internet. The communication means may include specialized connection devices for connecting to optical fiber, coaxial cable, Ethernet cabling, or other communication lines. Alternatively, wireless connections may be used, which may also include the use of suitable transmitters and receivers as is known in the art. Such wireless connectivity may include use of infra-red, RF, Bluetooth, or WiFi (IEEE 802.11b) communication means and the like. Additionally, the microprocessor 75 is commonly programmed using either embedded programming instructions or suitable software so that the microprocessor can carry out the tasks desired of it.

In one embodiment of the system and method of the present invention, the microprocessor 75 is capable of receiving signals from an upstream pressure sensor 105 through the input 85 (typically an amplifier and A/D converter). The upstream pressure sensor 105 is disposed adjacent an upstream infusion line so as to monitor the fluid pressure within the upstream infusion line, and provide signals representative of the sensed pressure within the infusion line to the microprocessor 75. The microprocessor 75, as described above, is programmed using appropriate software or embedded commands to analyze the signals received from the upstream pressure sensor 75. After analysis of the received upstream pressure signals is completed, the processor may output a signal through the output 90. This signal output may be directed to the pump motor 115 to control the infusion of fluid to the patient.

The output signal may also be directed to a display 120 to inform an operator of the status of the pump and/or the pressure within the upstream infusion line. This display may also include a means of providing a visual alert, such as a flashing display, blinking light, or a change in text color on the display to alert an operator that the infusion set-up requires attention.

The output signal may also be directed to an alert module 125. This alert module may be a separate module of the processor 75 that is controlling the pump 10, or it may be located at a location remote from the pump, and/or associated and in communication with a separate processor remote from the pump. The alert module 125 may be configured to provide visual, auditory, or a combination of visual and auditory notifications to care givers to alert the care giver that attention must be given to the infusion system. The alert module may produce signals that are communicated to consoles at the bed side, the nurse station, or a centrally located monitoring system. Additionally, various combinations of display changes and auditory alerts may be used to signify a priority of an alert, so that alerts which do not require immediate attention are less noticeable than alerts that require immediate attention to correct a problem before harm to the patient being infused can occur.

The alert module 125 may also provide signals representing the progress of the infusion, including any alerts generated due to a sensed reduced or negative pressure in the upstream infusion line 16 (FIG. 1), to a database where the information is stored for later inspection and analysis. The database may be associated with the pump 10, or the database may be remote from the pump. For example, where the pump is controlled by a remote programmer such as a wireless PDA, laptop, or tablet type computer, the database may be located and associated with the remote programmer. In another embodiment, the database may be part of an institutional information system which may be part of an enterprise wide network.

In another embodiment, the microprocessor 75 may also be configured to receive signals from a pump motor sensor 110 through the input 85. In this embodiment, the processor 75 may monitor the function of the pump, collecting, analyzing and storing information related to the infusion, such as, for example, the start time and completion time of the infusion, the amount of fluid infused, and the number of pump cycles that have been completed since the start of the infusion or since a selected time in the past. This information may be stored in the memory 80 for later retrieval and analysis, or the information may be communicated to another, remote, system using the communication means 95.

Figure 4:
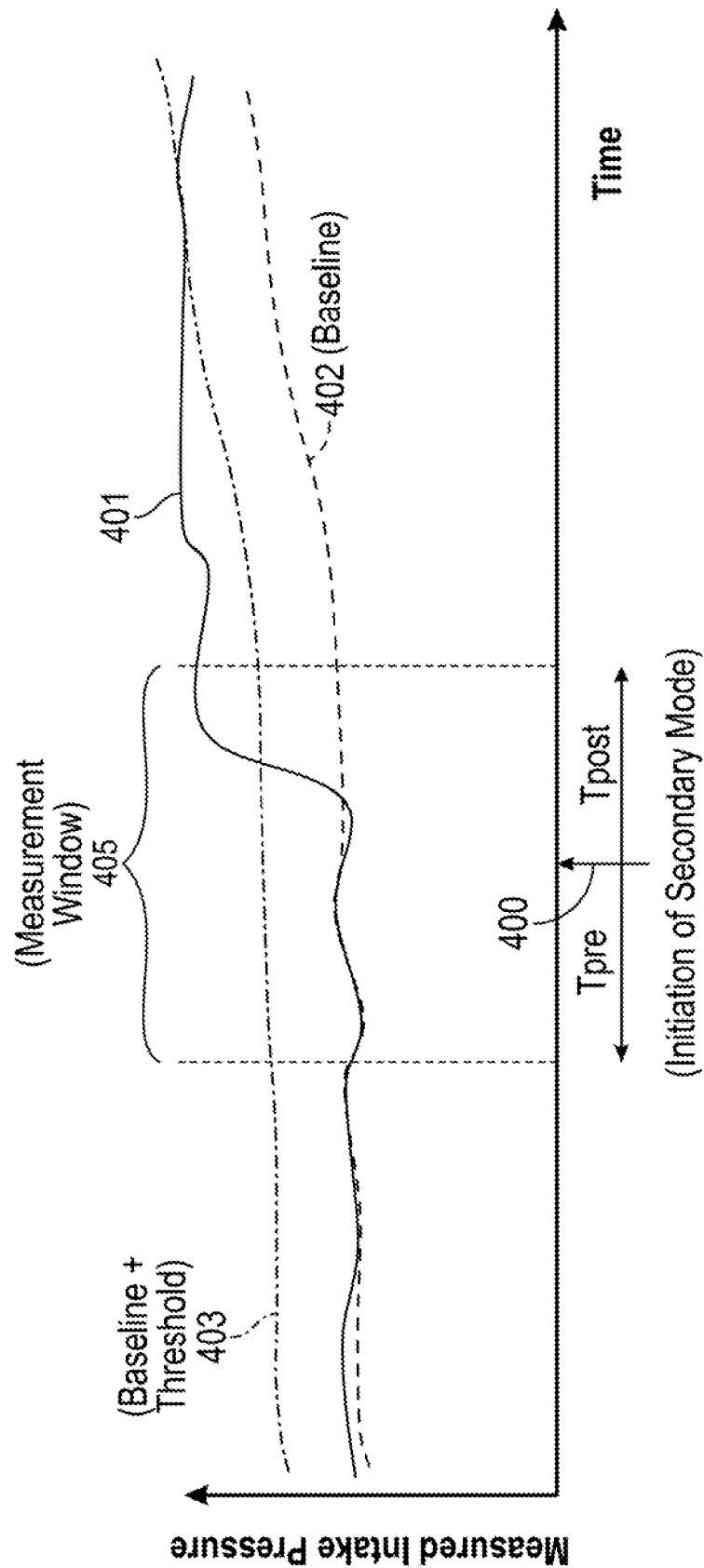
FIG. 4 is a graph showing the change in pressure over time of a secondary infusion administration.

One embodiment of the present invention includes a method for analyzing pressure changes detected within the upstream infusion line 16 (FIG. 1) to determine whether the secondary infusion is operating correctly. Referring to FIG. 4, there is illustrated a typical pressure profile as a function of time for the pressure within the upstream infusion line before and after initiation of a secondary infusion. As illustrated by the graph of FIG. 4 before a secondary infusion is initiated, the pressure within the upstream line 16 is relatively constant, and constitutes a baseline value. This pressure is proportional to the elevation (depth) of the primary fluid above the upstream pressure sensor. In a normal case, the caregiver first lowers the primary container relative to the secondary container establishing a pre-secondary infusion pressure baseline. The secondary infusion is initiated by opening of the manual clamp 28, the fluid within the secondary container 25 (FIG. 1) causes the pressure in the upstream line 16 to increase because the secondary container is typically positioned above the primary container, generally about eight inches above the primary container. This relative positioning of the containers results in the pressure below the check valve 29 in the upstream line 16 being higher than the pressure above the check valve by approximately 16 mmHg.

In FIG. 4, the signal 401 indicates the pressure over time. The arrow at 400 indicates the initiation of the secondary mode. To the left of arrow 400 is shown the pressure prior to secondary transition ("Tpre") and to the left of the arrow is shown the pressure after the secondary transition ("Tpost"). Numeral 404 indicates the secondary transition pressure rise. In particular, the difference in pressure caused by opening the manual valve 28 is reflected in FIG. 4 by a pressure rise 404. As will be discussed more fully below, the processor is programmed to sample the pressure signals provided by the upstream pressure sensor 50 (FIG. 2) associated with the infusion pump. As the pressure signals are sampled, the processor determines a continuously updating baseline pressure value 402, and stores that value in a memory for later use. The processor is also programmed to compare the sampled pressure value 401 with a computed signal consisting of the baseline value plus a threshold 403 to determine if the sampled pressure is increasing or decreasing a significant amount relative to the baseline 402. If the pressure value exceeds the baseline plus threshold value 403 within a selected period of time of initiation of the secondary infusion, here called the measurement window 405, the processor determines that the valve 28 of the secondary infusion line 26 has been opened and that the check valve 29 in the primary infusion line 16 is operating correctly. If a pressure rise is not observed during the measurement window, the processor determines that there is a fault with one or both valves in the infusion lines, or that the secondary container for some other reason is not draining correctly. If this condition is determined, an alert is provided to a care-giver indicating that attention must be given to the infusion set up. Alternatively, the condition is recorded, or stored in a storage media for further analysis or report generation.

Figure 5:
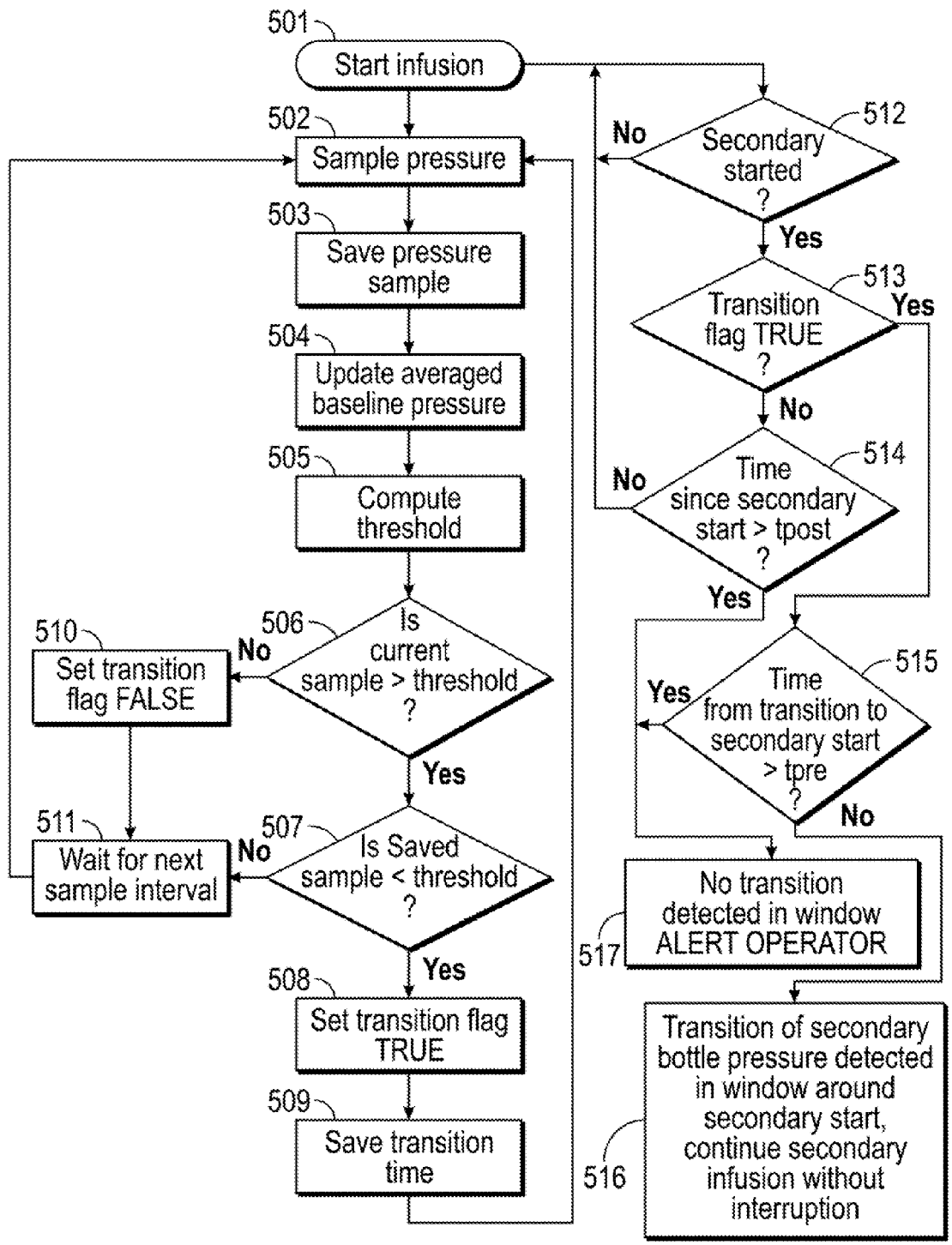
FIG. 5 is a flow chart illustrating the logic flow of one embodiment a passive monitoring program usable in a processor in accordance with aspects of the invention, and in a method in accordance with the present invention.

FIG. 5 is a flow diagram illustrating the logic of a method in accordance with the present invention. The infusion pump is started at box 501. It will be understood that carrying out the process of box 501 only serves as a start point, and that, rather than starting the pump, some other index of the beginning of the infusion, such as, for example, storing a start time in a memory, or starting a timer, may also be used.

Once the pump is started in box 501, the upstream line pressure is sampled in box 502. The sampled pressure may be stored in a memory dedicated to storing a baseline pressure value, as shown by box 504. The current sampled pressure is also stored 503 for use later in determining whether a transition of the secondary pressure has occurred indicating that the operator has properly positioned the secondary container 25 and opened the manual clamp 28. Alternatively, the pressure may be sampled for a period of time and averaged in ways known to those skilled in the art such as via a digital infinite impulse response low pass filter with a time constant of nominally three seconds. The baseline pressure value may be set to equal the digitally smoothed or averaged value. The baseline value is continually calculated and updated by the processor throughout the time the pump is operating as illustrated by the left side program flow of FIG. 5. Once a baseline value has been measured and processed, a threshold value is computed which is performed by adding a pre-defined threshold offset constant of typically 7-8 mmHg pressure to the baseline pressure in box 505. The current sampled pressure value is tested against this threshold value in decision box 506 to determine whether it exceeds the threshold. If it does exceed the threshold, then the previously saved valued 503 is checked to see if it was equal or less than the threshold at decision box 507. If both conditions are true, then the transition flag is set to true at box 508 and the time relative to the start of the infusion is stored at box 509. These values are used by the right-hand loop which concurrently tests for start of secondary infusions as described below. Setting of the transition flag to a true state indicates that the upstream pressure has transitioned from below to above the threshold indicating a rising upstream pressure of sufficient magnitude to demonstrate proper operation of the secondary fluid system. If the current pressure sample is not greater than the threshold in box 506, then the transition flag is set false in box 510 and the loop delays for the appropriate sample interval in box 511. If the saved sample is not equal or less than the threshold, then the loop delays for the appropriate sample interval and the flag and timers are not affected.

While the pressure is continuously sampled and tested in the left-hand loop of FIG. 5, the right-hand loop is used to check for initiation of secondary infusion mode, to determine whether a transition has occurred, and whether its occurrence is within the allowed time from the activation of the pump's secondary infusion mode. Detection of the activation of secondary mode occurs in box 512. Typically the operator will either have recently or will soon open valve 28 (FIG. 1) located in the secondary infusion line 26. In one embodiment of the present invention, the processor first determines whether the pressure signal was sampled within a selected time period, or window by performing the tests in boxes 514 or 515 depending on whether the transition occurred before or after the initiation of secondary infusion 513. If the time since start of secondary infusion exceeds the allowed window interval without detection of a transition as performed in box 514, or if a transition has occurred prior to initiation of secondary infusion but its occurrence was longer than the permitted window interval as performed by decision box 515 then an alert condition is generated in box 517. As shown in FIG. 4, the sampling window is a time period that is relative to the initiation of the secondary infusion. While the window illustrated in FIG. 4 shows the boundaries of the window centered on the initiation time of the secondary infusion, other boundaries may be used, such as starting the window at the starting time of the secondary infusion. This embodiment is advantageous in that it provides a filtering mechanism to filter out pressure changes in line 16 that occur due to factors other than the opening of valve 28 in line 26.

It will be understood that while the method of this embodiment of the present invention is described with reference to a sampled pressure, similar methods utilizing averaged pressure values may also be employed and are intended to fall within the scope of the present invention.

One possible disadvantage of the above described embodiment of the present invention which describes a passive monitoring system is that it requires use of a pressure sensor capable of detecting relatively small changes in line pressure. Additionally, in some cases, the differential in amount of fluid within the primary and secondary container may also reduce the pressure difference observed in a properly functioning secondary infusion. For example, in the case where the secondary container has a relatively large volume capacity making it tall vertically and is nearly empty, and the primary container is full, there may be only a minimal pressure increase in the primary line when the secondary valve is opened, and increase that may fall below the measurement sensitivity of the upstream pressure sensor or below the threshold offset constant thus being undetected by the passive detection logic system of FIG. 5.

In an alternative embodiment, the present invention includes what is termed an active method of monitoring the upstream pressure to determine whether a secondary infusion is operating properly. When a secondary infusion has been initiated and the valve 28 has been incorrectly left closed, the tubing region between the pump intake, the check valve 29, and the valve 28 is effectively closed to increasing volume since fluid cannot go through the check valve backwards. In this embodiment, a small volume of fluid, on the order of approximately 5 to 30 micro-liters, is infused into the upstream line 16 by operating the pump in reverse, causing a steep rise in the pressure within the line. When the pump resumes pumping into the patient, the pressure will fall rapidly. The pressure signal produced by such a momentary displacement of volume by the pump has a much larger mean value with respect to the pre-displacement average pressure. If the pressure increase exceeds a pre-determined threshold, a fault condition is determined to exist within the infusion set up and an alert is provided to the care-giver that attention should be given to the infusion set up. Alternatively, the pressure spike in the line may be induced by using an electromechanical actuator to squeeze and then release the infusion line. Either of these approaches may be automated using suitable programming commands to operate the processor to control the pump or actuator in the desired manner. Such an operation may be either manually controlled, such as, for example, by pressing a button on the pump to inject the bolus or activate the actuator, or it may be automated as part of the control programming of the processor.

In another embodiment, the pressure transient may be integrated with respect to the pre-test baseline. This integrated value is compared with a pre-determined threshold. If the integrated value exceeds the threshold, then a fault condition in the infusion set up is determined to exist, and an alert is provided to the care-giver that attention is required. In still other embodiments, other features of the intake pressure wave (the pressure transient within the upstream infusion line) transient response to the bolus, such as a peak to peak value magnitude of the wave, the mean frequency of the pressure wave, the width of the pressure wave, and the like, as are known to those skilled in the art, can be employed to determine whether a fault condition exists.

In the case where the valve 28 has been properly opened, the bolus will result in only a small pressure rise within the infusion line, because the secondary fluid will be able to flow backwards towards the secondary container. Such a pressure response will typically consist of an under-damped oscillatory wave with an average value of zero with respect to the pre-test pressure baseline.

Figure 6:
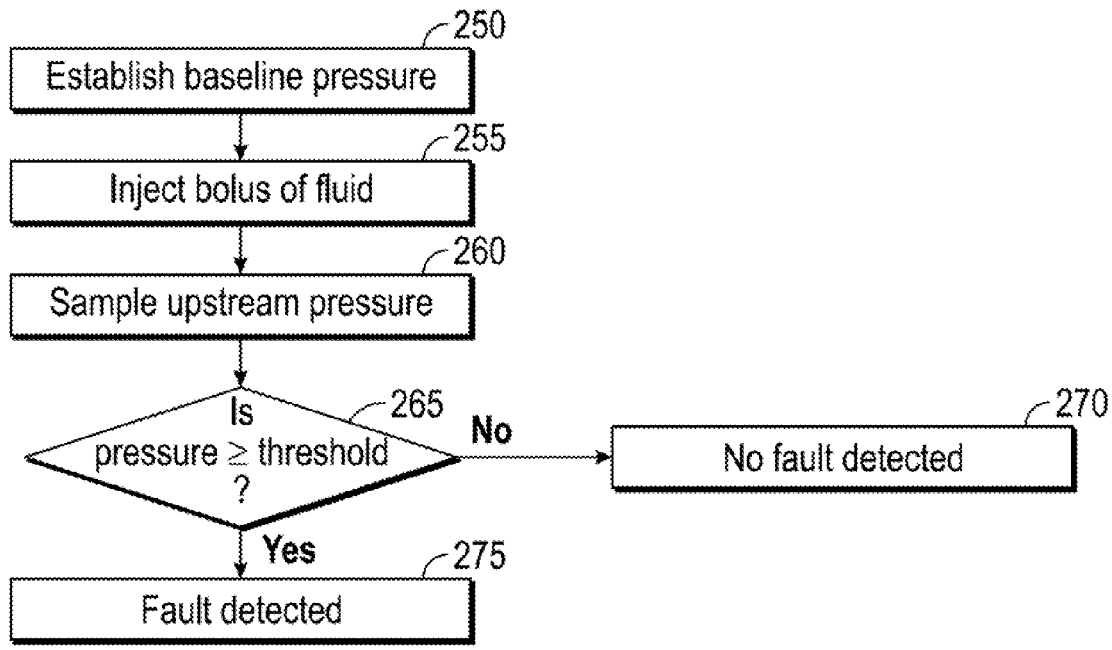
FIG. 6 is a flow chart illustrating the logic flow of one embodiment of an active monitoring program usable in a processor in accordance with aspects of the invention, and in a method in accordance with the present invention.

One embodiment of the present invention incorporating an active monitory process will now be described with reference to FIG. 6. In this embodiment, a baseline pressure is established in box 250 and bolus of fluid is injected into the upstream infusion line in box 255. The upstream pressure is sampled in box 260, and the sampled pressure is compared to a threshold pressure value in box 265. If the sampled pressure is lower than the threshold value, no fault is detected, as shown by box 270. If the sampled pressure is greater than or equal to the threshold pressure in box 265, a fault is determined in box 275 to exist in the infusion set up. The processor may provide an alert to the care-giver indicating that a fault in the infusion set up exists that requires attention and correction.

Figure 7:
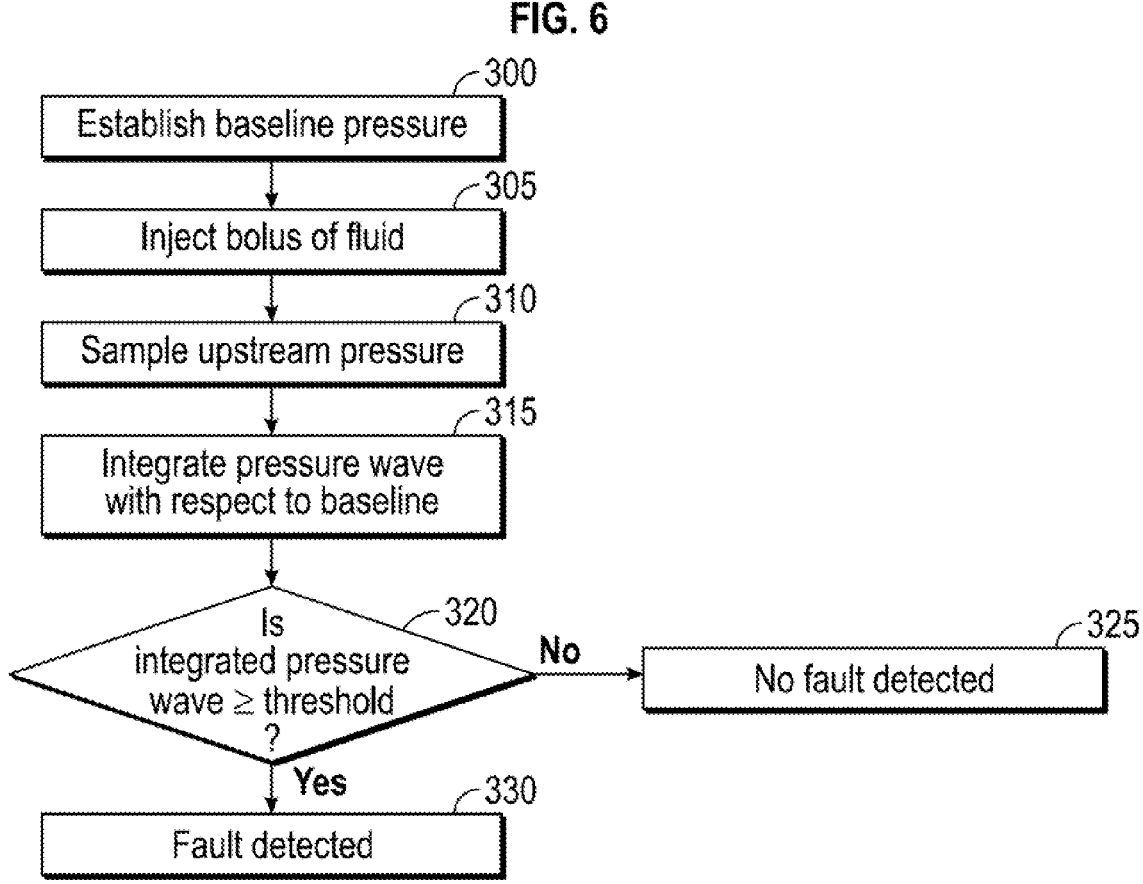
FIG. 7 is a flow chart illustrating the logic flow of another embodiment of an active monitoring program usable in a processor in accordance with aspects of the invention, and in a method in accordance with the present invention.

FIG. 7 is a flow chart illustrating another embodiment of the present invention. In this embodiment, a baseline pressure is established in box 300, and a bolus of fluid is injected into the upstream infusion line in box 305, as described previously. The upstream pressure is sampled in box 310, and the pressure wave sampled is integrated in box 315 with respect to the baseline pressure value established in box 300. If the integrated pressure wave is equal to or exceeds a predetermined threshold, as shown in box 320, a fault is determined to exist, as illustrated by box 330. If the integrated pressure wave is smaller than the threshold, a no fault condition is determined to exist, as shown in box 325.

In some pumping mechanisms, such as, for example, a multi-finger linear peristaltic pump, the pump reversal to create the bolus results in a temporary "test" operation whose effect on both the intake and output fluid pathways is easily and rapidly undone by placing the pump back into normal forward flow and re-infusing the test volume plus an additional volume to ensure that the very small amount of blood that is aspirated from the patient's vein is immediately, typically within one second or less, restored and the catheter is re-flushed. This operation is similar to manual procedures routinely performed by care-givers using a syringe to check for patency of an infusion line. Some pumping mechanisms such as piston type infusion pumps may be controlled to isolate control of flow at the intake side from the output side, permitting the reverse flow test to be performed with little or no flow change at the output of the pump.

In some cases, any momentary reversal of the flow of the pump may not be desirable such as in a very low flow rate infusion of highly concentrated, rapid acting medications. Fortunately, secondary infusions are commonly performed at a high infusion rate, such as, for example, 100 milliliters per hour. In such a case, a 30 microliter bolus would be the equivalent of the flow produced in one second and thus have no untoward clinical impact. Secondary infusions are very rarely used for low flow rate pediatric or neonatal infusions, especially of short half-life medications. Nonetheless, the various embodiments of the present invention may be combined to mitigate any concern over using a bolus to determine if the infusion set up is operating correctly.

In this embodiment, the passive monitoring embodiment of the present invention is performed as a default. In the case that the passive monitoring method detects an adequate pressure rise indicating that the secondary manual valve 28 (FIG. 1) is open, then the active method would not be used, since it would not be necessary. However, in the case where passive monitoring using the present invention indicates a fault condition, an embodiment of the present invention utilizing the active monitory method or methods described above may be utilized to confirm the result of the passive monitory test. It is believed that based on typical containers and practices used that combining the passive and active monitoring embodiments of the present invention in this manner would reduce the need to inject a bolus by reversing the pump to a small percentage of infusions. Additionally, if the active method determined that the secondary line valve 28 was open, the operator could be prompted by the processor to increase the height of the secondary container or lower the primary container to increase differential pressure. Where several secondary infusions are planned, increasing the height difference between the primary and secondary containers in this manner would likely ensure that use of the active method in subsequent infusions would be reduced or eliminated entirely, since the increased container height would increase the pressure differential in the infusion line, resulting in a higher probability that the passive method would detect a properly functioning secondary infusion.

The above described embodiments of the present invention are useful for detecting when the secondary infusion valve is not opened, resulting in little or no flow through the secondary infusion line. The combination of passive and active monitoring methods in accordance with the present invention is also useful for determining the existence of other types of fault conditions within the infusion set up. For example, where the valves are operating correctly, but the secondary container is positioned below the primary container, the passive monitoring will fail to detect a pressure increase, but the active method will determine that a normal condition exists, since the bolus will not result in a pressure increase in the line, since fluid will be able to flow backwards towards the secondary container. In this case, the processor may be programmed to interpret a negative passive result and a positive active result as a potential problem, and provide an alert, such as, for example, a "CHECK SETUP" or similar message to the care-giver.

A similar situation will exist where the check valve 29 (FIG. 1) fails, allowing fluid to flow upwards towards the primary container. Again, the passive monitoring method would provide a negative result, even if the secondary valve 28 is opened, because the pressure sensor remains limited by the height of the fluid in the primary container preventing a pressure rise from occurring upon opening of valve 28. The active method would provide a positive result, that is, an indication that the infusion was normal, for the same reason. This inconsistent set of test results, failure of the passive and success of the active tests would again be interpreted by the processor as requiring attention by the care-giver, and an alert would be provided. The same interpretation would be made by the processor, for the same reasons, in the case where a double fault condition existed, such as when the valve 28 is not opened within the allowed window and the check valve 29 is faulty, permitting flow upwards into the primary container during the secondary infusion. Again, the passive test will fail and subsequent active test produce a positive result. These inconsistent results would initiate an alert to the care-giver.

A fault condition may also arise when the secondary container is over- or under-filled. As the secondary container empties during a secondary infusion, the cross-sectional area of the wetted surface of the secondary container decreases. When the secondary container is completely empty, this area suddenly reduces to the area of the drip chamber cannula associated with the secondary container, once the fluid/air surface passes the cannula, the area slightly increases to that of the drip chamber. When the drip chamber empties, the cross-sectional area changes to the cross-sectional area of the infusion tubing. An inverse correlation exists between these cross-sectional area changes and the rate of pressure change with respect to the volume withdrawn from the container and infusion set.

Typically, a drip chamber is filled with at least 2 ml of fluid. Large volume parenteral pumps typically produce fluid flow in cycled produced by the peristaltic mechanism of the pump, the cycles typically being on the order of 0.15 to 0.25 ml. In another embodiment of the present invention, the fill state of the secondary container may be determined by measuring the mean pressure in each of four sequential pumping cycles comprising typically less than 1 ml of fluid volume. The mean intake pressure of the most recent (Pavg (n)) and fourth most recent (Pavg(n−3)) cycles are compared by the processor to determine if the rate of change of pressure has increased above a pre-determined threshold. The processor accomplishes this comparison by the computing a slope, $\Delta P/\Delta V$ according the following equation defining the slope of the pressure-volume relationship:

$$\frac{\Delta P}{\Delta V} = \frac{P\ AVG(n-3) - P\ AVG(n)}{3 \cdot V_{cycle}}$$

If the slope of the pressure-volume relationship exceeds the threshold, then one of several actions may be taken depending on the volume infused relative to the programmed secondary volume to be infused value. If the secondary volume infused is less than an underfill volume for the container, or if the volume infused is greater than an overfill volume for the container, the processor provides an alert to the care-giver that the infusion set requires attention. Additionally, if programmed to do so, the processor may stop the pump, halting the infusion until the condition is confirmed and corrected by the care-giver. If the volume infused is between the underfill volume and the overfill volume for the container at the time an empty container is detected, the processor determines that no fault condition exists, and continues the infusion in accordance with its programming, which may include automatically switching to primary mode at a rate appropriate for infusion of the primary infusion fluid.

While several particular forms of the invention have been illustrated and described, it will be apparent that various modifications can be made without departing from the spirit and scope of the invention.

We claim:

1. A method for passively detecting a fault condition in an intravenous (IV) set having a primary line coupled to a first fluid source, a secondary line coupled from a second fluid source to a fitting, upstream of a pumping mechanism, on the primary line, a check valve in the portion of the primary line between the first fluid source and the fitting, a valve in the portion of the secondary line between the second fluid source and the fitting, and a portion of the primary line that is downstream of the fitting being coupled to the pumping mechanism of an infusion pump, the method comprising:

determining with a processor a window of time around an initiation time of a secondary infusion mode;

generating a series of pressure measurements by measuring a pressure of a fluid in the primary line at a point between the fitting and the pumping mechanism at periodic intervals;

generating one or more most-recent pressure measurements by measuring the pressure of the fluid in the primary line at the point between the fitting and the pumping mechanism within the window of time;

calculating a threshold pressure for each of the one or more most-recent pressure measurements based on the series of pressure measurements prior to the respective most-recent pressure measurement;

comparing the each of the one or more most-recent pressure measurements to the respective threshold pressure; and indicating a fault condition if none of the one or more most-pressure measurement exceeds the threshold within the window of time.

2. The method of claim 1, wherein the series of pressure measurements generated by measuring a pressure of a fluid in the primary line at a point between the fitting and the pumping mechanism at periodic intervals is generated prior to the initiation time of the secondary infusion mode.

3. The method of claim 1, wherein second fluid source is elevated higher than the first fluid source by a certain elevation.

4. The method of claim 3, wherein a pressure of the fluid in the portion of the primary line that is downstream of the fitting is proportionately greater than a pressure of the fluid in the secondary line according to the certain elevation.

5. The method of claim 4, wherein the pressure of the fluid in the portion of the primary line that is downstream of the fitting is approximately 16 mmHg more than the pressure of the fluid in the secondary line.

6. The method of claim 1, wherein the threshold pressure for each of the one or more most-recent pressure measurements is equal to a sum of a respective one of the series of pressure measurements with a threshold offset constant.

7. The method of claim 6, wherein the threshold offset constant is at least 7 mmHg.

8. The method of claim 1, wherein each of the series of pressure measurements comprises a pressure sampled for a period of time and averaged via low pass filter.

9. The method of claim 1, wherein the series of pressure measurements is regularly updated prior to the initiation time of the secondary infusion mode.

10. The method of claim 1, further comprising indicating the fault condition if each of the one or more most-pressure measurement exceeds the threshold for greater than the window of time.

11. A system for passively detecting a fault condition in an intravenous (IV) set having a primary line coupled to a first fluid source, a secondary line coupled from a second fluid source to a fitting, upstream of a pumping mechanism, on the primary line, a check valve in the portion of the primary line between the first fluid source and the fitting, a valve in the portion of the secondary line between the second fluid source and the fitting, and a portion of the primary line that is downstream of the fitting being coupled to the pumping mechanism of an infusion pump, the system comprising:

a pumping mechanism operatively coupled to a portion of the primary line that is downstream of the fitting, the pumping mechanism configured to selectably cause a fluid to flow within the primary line;

a pressure sensor operatively coupled to the primary line at a point between the fitting and the pumping mechanism, the pressure sensor configured to measure a pressure of a fluid within the primary line and provide pressure measurements; and a processor coupled to the pumping mechanism and the pressure sensor, the processor configured to:
  determine a window of time around an initiation time of a secondary infusion mode;
  generate a series of pressure measurements by measuring a pressure of a fluid in the primary line at a point between the fitting and the pumping mechanism at periodic intervals;
  generate one or more most-recent pressure measurements by measuring the pressure of the fluid in the primary line at the point between the fitting and the pumping mechanism within the window of time;
  calculate a threshold pressure for each of the one or more most-recent pressure measurements based on the series of pressure measurements prior to the respective most-recent pressure measurement;
  compare the each of the one or more most-recent pressure measurements to the respective threshold pressure; and
  indicate a fault condition if none of the one or more most-pressure measurement exceeds the threshold within the window of time.

12. The system of claim 11, wherein the series of pressure measurements generated by measuring a pressure of a fluid in the primary line at a point between the fitting and the pumping mechanism at periodic intervals is generated prior to the initiation time of the secondary infusion mode.

13. The system of claim 11, wherein second fluid source is elevated higher than the first fluid source by a certain elevation.

14. The system of claim 13, wherein a pressure of the fluid in the portion of the primary line that is downstream of the fitting is proportionately greater than a pressure of the fluid in the secondary line according to the certain elevation.

15. The system of claim 14, wherein the pressure of the fluid in the portion of the primary line that is downstream of the fitting is approximately 16 mmHg more than the pressure of the fluid in the secondary line.

16. The system of claim 11, wherein the threshold pressure for each of the one or more most-recent pressure measurements is equal to a sum of a respective one of the series of pressure measurements with a threshold offset constant.

17. The system of claim 16, wherein the threshold offset constant is at least 7 mmHg.

18. The system of claim 11, wherein each of the series of pressure measurements comprises a pressure sampled for a period of time and averaged via low pass filter.

19. The system of claim 11, wherein the series of pressure measurements is regularly updated prior to the initiation time of the secondary infusion mode.

20. The system of claim 11, wherein the processor is also configured to indicate the fault condition if each of the one or more most-pressure measurement exceeds the threshold for greater than the window of time.

\* \* \* \* \*